US010631783B2

(12) United States Patent
Persson

(10) Patent No.: US 10,631,783 B2
(45) Date of Patent: Apr. 28, 2020

(54) METHOD AND A SYSTEM FOR MONITORING HEALTHCARE GARMENTS

(71) Applicant: HealthTextiles i Sverige AB, Gävle (SE)

(72) Inventor: Tomas Persson, Gävle (SE)

(73) Assignee: Health Textiles i Sverige AB (SE)

( * ) Notice: Subject to any disclaimer, the term of this patent is extended or adjusted under 35 U.S.C. 154(b) by 48 days.

(21) Appl. No.: 16/060,507

(22) PCT Filed: Dec. 8, 2016

(86) PCT No.: PCT/SE2016/051230
§ 371 (c)(1),
(2) Date: Jun. 8, 2018

(87) PCT Pub. No.: WO2017/099658
PCT Pub. Date: Jun. 15, 2017

(65) Prior Publication Data
US 2018/0360381 A1 Dec. 20, 2018

(30) Foreign Application Priority Data
Dec. 11, 2015 (SE) .................. 1551631

(51) Int. Cl.
*A61B 5/00* (2006.01)
*A61B 5/01* (2006.01)
(Continued)

(52) U.S. Cl.
CPC .......... *A61B 5/6804* (2013.01); *A61B 5/0008* (2013.01); *A61B 5/01* (2013.01);
(Continued)

(58) Field of Classification Search
CPC ....... A61B 5/01; A61B 5/6802; A61B 5/6804; A61B 2562/0271; A61B 5/0008;
(Continued)

(56) References Cited

U.S. PATENT DOCUMENTS 5,635,909 A * 6/1997 Cole .................... A62B 17/003
340/586
8,930,147 B2 1/2015 Pollack et al.
(Continued)

FOREIGN PATENT DOCUMENTS

| CA | 2770325 | 8/2010 |
|---|---|---|
| WO | 2011072837 A1 | 6/2011 |
| WO | 2013006644 A1 | 1/2013 |

OTHER PUBLICATIONS

Office Action for Application No. 1556131-3, dated Jul. 7, 2016, 5 pages, The Swedish Patent Office. X.
(Continued)

*Primary Examiner* — Max F Hindenburg
(74) *Attorney, Agent, or Firm* — McDonald Hopkins LLC

(57) ABSTRACT

A method and a system for monitoring healthcare garments (3), wherein the method comprises the steps of:
providing a temperature sensor (1) on or in a healthcare garment,
sensing the temperature of the healthcare garment by means of the temperature sensor,
transferring temperature data relating to the sensed temperature over at least one network (5) and a wireless interface (7) from the temperature sensor to a base station (4), and
based on the transferred temperature data, determining information relating to a usage cycle of said healthcare garment.

10 Claims, 1 Drawing Sheet

(51) Int. Cl.
*G16H 40/20* (2018.01)
*G16H 40/67* (2018.01)
*G16H 40/63* (2018.01)
*G06Q 50/22* (2018.01)
*G16H 40/40* (2018.01)
*G08B 21/24* (2006.01)

(52) U.S. Cl.
CPC .............. *A61B 5/746* (2013.01); *G06Q 50/22* (2013.01); *G16H 40/20* (2018.01); *G16H 40/63* (2018.01); *G16H 40/67* (2018.01); *A61B 2505/03* (2013.01); *G08B 21/24* (2013.01); *G16H 40/40* (2018.01)

(58) Field of Classification Search
CPC .............. G01K 13/002; G06K 19/027; G06K 19/0717; G16H 40/40
See application file for complete search history.

(56) References Cited

U.S. PATENT DOCUMENTS

| | | | | |
|---|---|---|---|---|
| 2004/0116822 A1* | 6/2004 | Lindsey | ................ | G01K 1/024 600/549 |
| 2005/0054941 A1* | 3/2005 | Ting | .................... | A61B 5/0408 600/529 |
| 2006/0125623 A1* | 6/2006 | Appelt | ............... | A61B 5/02055 340/521 |
| 2006/0235328 A1* | 10/2006 | Willis | ..................... | G01K 1/02 600/549 |
| 2012/0136231 A1* | 5/2012 | Markel | ................ | A61B 5/0015 600/388 |
| 2012/0218123 A1 | 8/2012 | Lusheng et al. | | |
| 2013/0274587 A1* | 10/2013 | Coza | .................... | A61B 5/6804 600/409 |
| 2014/0097944 A1* | 4/2014 | Fastert | ................ | G06K 19/027 340/10.51 |
| 2015/0148681 A1 | 5/2015 | Abreu | | |

OTHER PUBLICATIONS

Final Notice for Application No. 1556131-3, dated Apr. 26, 2018, 20 pages, The Swedish Patent Office.
Standardization for Smart Clothing Technology, Network and Parallel Computing; Springer International Publishing, Cham, published Jul. 19, 2009; doi: 10.1007/978-3-642-02580-8_84; abstract; section 4 (Case Study).
International Search Report dated Feb. 21, 2017; International Patent Application No. PCT/SE2016/051230 filed Dec. 8, 2016; ISA/SE.
Canadian Patent Office, PPH Acceptance Patent Application No. 3,007,966 drafted Mar. 11, 2019.
Office Action dated Nov. 28, 2019; Canadian Application No. 3,007,966.

* cited by examiner

METHOD AND A SYSTEM FOR MONITORING HEALTHCARE GARMENTS

CROSS-REFERENCE TO RELATED APPLICATION

This application is a 35 U.S.C. 371 national stage filing of PCT Application No. PCT/SE2016/051230 filed on Dec. 8, 2016, entitled "A METHOD AND A SYSTEM FOR MONITORING HEALTHCARE GARMENTS," which claims priority to Swedish Application No. 1551631-3, filed on Dec. 11, 2015, each of which are incorporated herein in their entirety by reference.

FIELD OF THE INVENTION

The present invention relates to a method for monitoring healthcare garments according to the preamble of claim 1. It further relates to a system for monitoring healthcare garments according to the preamble of claim 9.

BACKGROUND AND PRIOR ART

Nosocomial infections, also called hospital acquired infections, have become a large problem in modern healthcare. Such infections include e.g. urinary infections, surgical site infections, pneumonia, and bacteraemia. These infections are important causes of morbidity and mortality and form a significant burden for healthcare systems all over the world.

A major focus for hospitals and other healthcare institutions is therefore to reduce or eliminate such hospital acquired infections. One strategy for preventing hospital acquired infections is to limit transmission of organisms between patients in direct patient care through e.g. adequate handwashing, glove use, and laundry of healthcare garments. Regular washing of healthcare garments, i.e. garments worn by healthcare staff, using a correct washing cycle, is of great importance for prevention of hospital acquired infections. For example, it is often desirable that healthcare garments are washed after one work shift. However, many hospitals have identified problems associated with laundry, such as e.g. difficulties in ensuring that the healthcare garments are washed after each work shift instead of being stored until the next work shift and reused.

SUMMARY OF THE INVENTION

It is an objective of the present invention to provide a method and a system that can contribute to overcoming the above mentioned problems and help preventing spread of hospital acquired infections via healthcare garments.

This objective is, in a first aspect of the present invention, achieved by the initially defined method, which is characterised in that it comprises the steps of:
sensing the temperature of a healthcare garment by means of a temperature sensor provided on or in the healthcare garment,
transferring temperature data relating to the sensed temperature over at least one network and a wireless interface from the temperature sensor to a base station, and
in the base station, based on the temperature data, determining information relating to a usage cycle of said healthcare garment.

By sensing and communicating the temperature of healthcare garments, it is possible to obtain information relating to the usage cycle of the healthcare garment, such as the time elapsed since a most recent wash, the number of times that the healthcare garment has been worn without intermediate wash, a body temperature of a wearer of the healthcare garment, a time at storage, a washing temperature used, etc. This makes it possible for a hospital or healthcare institution to monitor its stock of healthcare garments and identify any problems associated with the usage cycles of the healthcare garments that may lead to an increased risk of spreading germs. Monitoring may be carried out on an individual level, identifying each healthcare garment, or on a stock level, identifying e.g. a percentage of the monitored healthcare garments that have been washed between two different wearing occasions. In this case, it is possible to carry out the monitoring completely anonymously, without identifying individual wearers.

The sensor used should be small and versatile, and it should also be able to withstand washing at a desired washing temperature, usually at least 70° C. It can be integrated with a fabric of the healthcare garment or mounted separately on the healthcare garment, e.g. in a hem of the healthcare garment, such as in a neckband or in a sleeve hem. It is preferable that the sensor is energy efficient to ensure a long battery life. The sensor may for this purpose be configured to communicate temperature data to the base station only once a day or even more seldom. Conditions may be set that rule the sending of temperature data. The sensor may e.g. check for a connection to the wireless network at a predetermined time or after having collected a certain amount of data, and only then send the collected data. The sensor may also be configured so that it only registers large changes in temperature, such as when a wearer puts on a healthcare garment and the temperature changes from a storage temperature of about 20° C. to a wearing temperature of about 37° C., or when the washing temperature is reached.

According to one embodiment of the invention, the step of determining information relating to the usage cycle of the healthcare garment includes comparing the temperature data to at least one predefined temperature value or temperature range associated with a specified usage category. Such a usage category can be e.g. wearing, washing, storing, wearing by infected wearer, etc. By comparison with predefined temperature values or ranges, a fast and efficient categorisation of the healthcare garment's usage can be achieved.

According to one embodiment of the invention, said at least one predefined temperature value or temperature range associated with a specified usage category includes at least one of a predefined wearing temperature range, a predefined washing temperature value, a predefined storage temperature range, and an infection indicating temperature range. By defining a wearing temperature range corresponding to the expected temperature of the healthcare garment when worn, a wearing time of the healthcare garment can be determined. A washing temperature value can be set to determine if a healthcare garment has been washed at a correct temperature. Washing of healthcare garments is often carried out by external service providers, and it is therefore useful for the hospital or healthcare institution to be able to control that provisions regarding the washing temperature are respected. The washing temperature value or range can also be used to identify whether a healthcare garment has been washed between work shifts or at prescribed intervals. A storage temperature range, corresponding to an expected temperature of the healthcare garment during storage can be defined to determine a time at storage of the healthcare garment. An infection indicating temperature range is preferably set to slightly higher than a wearing temperature range, so that it is possible to determine if a wearer of the healthcare garment has an elevated body temperature, thus indicating infection.

According to one embodiment of the invention, the step of determining information relating to the usage cycle of the healthcare garment includes determining the amount of time spent in said wearing temperature range and/or in said storage temperature range without exceeding said washing temperature value. It can thus easily be determined whether the healthcare garment has been worn or stored for too long without washing.

According to one embodiment of the invention, said information relating to the usage cycle of said healthcare garment includes a body temperature of a wearer of said healthcare garment. By determining the body temperature of the wearer of healthcare garments, it can at an early stage be identified if the wearer, such as a nurse, a surgeon, or a physician, has an infection.

According to one embodiment of the invention, the information relating to a usage cycle of said healthcare garment is determined solely based on data received from the temperature sensor. Thus, a tag Thereby, no data from any additional devices, such as an RFID (radio frequency identification) tag is necessary to determine information relating to the usage cycle. Apart from the temperature sensor, no device configured to communicate with the base station needs to be provided on or in the healthcare garment in this embodiment. Since the battery time of the temperature sensor may often be longer than e.g. the battery time of an RFID tag, this may lead to less maintenance and an improved reliability of the method. Furthermore, experienced violations of the personal integrity of the healthcare staff can be avoided, since the healthcare garments do not need to be associated with individual wearers of the healthcare garment.

According to one embodiment of the invention, the method further comprises the steps of:
  comparing said information relating to a usage cycle of said healthcare garment to at least one predefined warning condition, and
  given that said predefined warning condition is fulfilled, generating an error code.

A warning condition may be set relating to e.g. washing temperature, time of wear, body temperature of wearer, etc. By generating an error code if a warning condition is fulfilled, it is possible to easily identify any unwanted usage of the healthcare garment, such as washing at too low temperature or wearing the healthcare garment for too long without washing.

According to one embodiment of the invention, the method further comprises the steps of:
  communicating said error code to a warning indicator provided on or in said healthcare garment, and
  in response to said error code, emitting a warning signal from the warning indicator.

The warning indicator can be e.g. a light-emitting diode (LED) or similar, indicating visually that there is a potential problem with contamination associated with the healthcare garment or the wearer of the healthcare garment. In this way, it is easy to identify for a wearer of the healthcare garment or for other persons that the healthcare garment needs to be deposited for washing. The warning indicator can also be configured to emit an audio warning signal. The warning signal may further be emitted only as a specific condition is fulfilled, such as when the healthcare garment is put on by a wearer after storage.

According to another aspect of the present invention, the above mentioned objective is achieved by means of the initially defined system, characterised in that it comprises:
  a temperature sensor provided on or in a healthcare garment, the temperature sensor being adapted to sense the temperature of said healthcare garment and to send temperature data relating to the sensed temperature over at least one network and a wireless interface, and
  a base station adapted to receive said temperature data, wherein the base station is configured to, on the basis of the received temperature data, determine information relating to a usage cycle of said healthcare garment.

Advantages as well as preferred embodiments of such a system are apparent from the above above discussion relating to the proposed method.

According to one embodiment of this aspect of the invention, the base station is configured to compare said information relating to a usage cycle of said healthcare garment to at least one predefined warning condition, and given that said predefined warning condition is fulfilled, generate an error code.

According to another embodiment, the system further comprises a warning indicator provided on or in said healthcare garment, the warning indicator being configured to receive said generated error code from the base station and in response thereto emit a warning signal.

According to one embodiment, the temperature sensor is mounted in a neckband of the healthcare garment. This is a suitable position for the sensor.

It is of course also possible to combine the system according to the invention with an RFID (radio frequency identification) system for tracking and individually identifying healthcare garments, if individual monitoring of healthcare garments is desired. By combining the information determined using the proposed method with information obtained using a RFID system, having RFID tags mounted on each healthcare garment, it is possible for a particular healthcare unit to obtain a detailed follow-up on the usage of the healthcare garments associated with that particular healthcare unit and identify problems that may lead to spread of hospital acquired infections. However, the RFID system is preferably provided separately from the system according to the invention, such that e.g. battery life of the temperature sensors are not affected by an RFID system. In this way, monitoring of healthcare garments can be carried out without relying on a functioning RFID system.

Further advantages as well as advantageous features of the present invention will appear from the following detailed description.

BRIEF DESCRIPTION OF THE DRAWINGS

Embodiments of the invention will in the following be described with reference to the appended drawings, in which.

DETAILED DESCRIPTION OF EMBODIMENTS OF THE INVENTION

Figure 1:
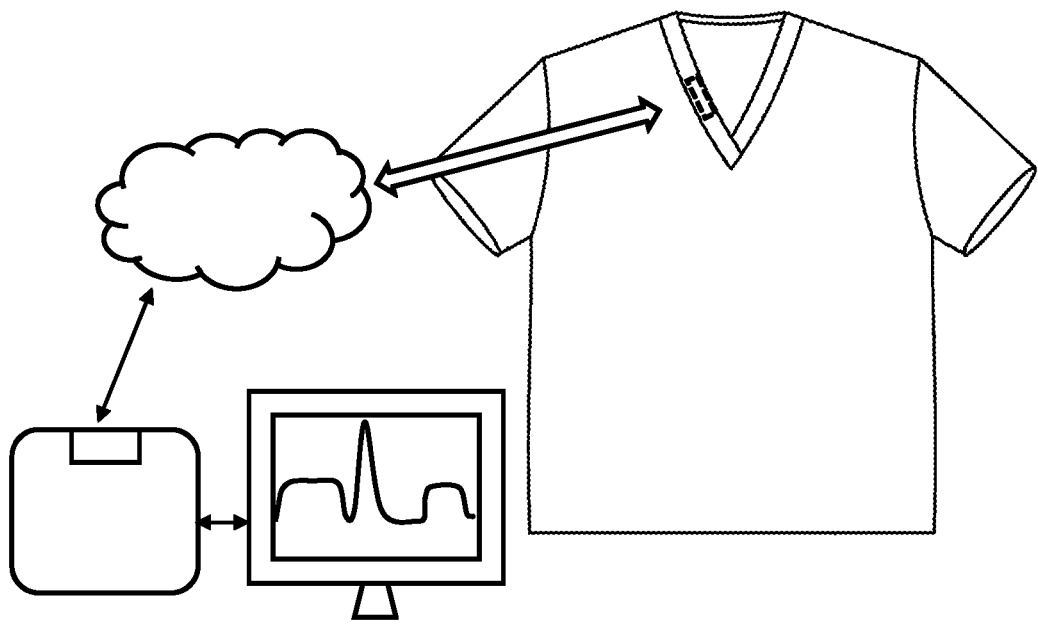
FIG. 1 schematically shows a system according to an embodiment of the invention.

A system according to an embodiment of the invention is schematically shown in FIG. 1. The system comprises a plurality of temperature sensors 1, each mounted in a neckband 2 of a healthcare garment 3. Each temperature sensor 1 is configured to sense the temperature of the healthcare garment 3 and to send a data message DM comprising temperature data corresponding to the sensed temperature to a central base station 4 via a wireless network 5. The base station 4 has a primary interface 6 toward the wireless network 5 and the wireless network 5 in turn has a secondary interface 7, configured to communicate wirelessly with the temperature sensor 1. The base station 4 comprises a data storage medium 8 on which temperature data are stored in a database and a processing unit 9 configured to process the temperature data and determine information relating to a usage cycle of the monitored healthcare garment 3 or healthcare garments. Display means 10, here comprising a screen 11, is provided for displaying the determined information in the form of e.g. a graph 12 showing temperature as a function of time.

Figure 2:
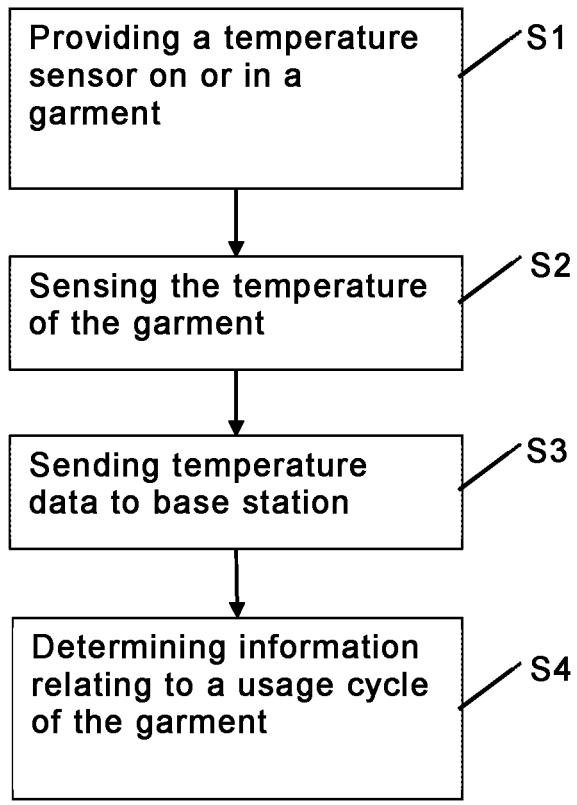
FIG. 2 is a flow chart illustrating a method according to an embodiment of the invention.

A method according to an embodiment of the invention, using the system shown in FIG. 1, is illustrated in FIG. 2. In a first step S1, the temperature sensor 1 is provided on or in the healthcare garment 3, such as in a neckband 2 of the healthcare garment. In a second step S2, the temperature of the healthcare garment 3 is sensed by means of the temperature sensor 1. This can be performed regularly at a predetermined frequency, but the sensor may also be configured such that it only senses or records large changes in temperature, such as a change from 20° C. to 35° C., indicating that the healthcare garment 3 is taken from a storage and put on by a wearer. As long as the temperature is constant or only varies by a small amount, the sensor does not collect any new data. As the temperature changes by a large amount, the sensor records a new temperature value and a point in time at which the change occurs. Temperature data relating to the sensed temperature are in a step S3 sent in a data message DM over the wireless network 5 and the primary and secondary interfaces 6, 7 from the temperature sensor 1 to the base station 4. Based on the transferred temperature data, information relating to a usage cycle of the healthcare garment 3 is determined in a step S4. This information can thereafter be displayed using the display means 10, e.g. in the form of a graph 12 or a diagram. For example, it is possible to show temperature of the healthcare garment 3 as a function of time, or time spent in a certain usage category such as wear or storage, a time since last wash, etc. Information relating to several healthcare garments 3 can be compiled and displayed in e.g. a histogram or the like. Any kind of suitable software can be used to analyse, compile and present the data and information derived therefrom.

In one example, the method and system according to the invention are used to monitor a large amount of healthcare garments in a hospital. Each healthcare garment 3 is provided with a temperature sensor 1 as described above and a base station 4, to which temperature data are communicated, is provided in the hospital. Each temperature sensor 1 senses and sends temperature data associated with the healthcare garment 3 on which the sensor 1 is provided to the base station 4. Temperature data may preferably be temporarily stored in the temperature sensor 1 and sent in a batch to the base station 4, e.g. once a day. In the base station 4, the received temperature data are compared to several predefined temperature values and temperature ranges associated with specified usage categories. In the example, a wearing temperature range of 32° C.-37° C., indicating that a person is wearing the healthcare garment 3, and a washing temperature value of 72° C. are defined. When the temperature of the healthcare garment 3 falls within the wearing temperature range, the healthcare garment 3 is categorised as being worn by a wearer. When the temperature of the healthcare garment 3 exceeds the washing temperature value, it is categorised as being washed. When the temperature is below the wearing temperature range, the healthcare garment is categorised as being stored. Further temperature ranges or temperature values can also be predefined, relating to e.g. an infection indicating temperature range or value which is characteristic for an infected wearer having a body temperature of more than 37° C., an insufficient washing temperature value or range of less than 72° C., or a storage temperature range.

In one embodiment of the system and the method according to the invention, the processing unit 9 in the base station 4 is configured to generate error codes if certain predefined warning conditions are fulfilled. The warning conditions are set so that fulfillment thereof may lead to spread of hospital acquired infections via the healthcare garments 3. Such a warning condition can be e.g. that an insufficient washing temperature has been used, such as a washing temperature of less than 70° C. Another warning condition can be that the healthcare garment 3 has been worn for too long without washing, i.e. has been within a wearing temperature range for a time period exceeding a predetermined threshold value. Another warning condition can be set so that an error code is generated if the healthcare garment 3 is put on by a wearer twice without intermediate wash, i.e. if the temperature lies within the wearing temperature range twice without reaching a washing temperature value or range in between. Yet another warning condition can be set so that an error code is generated if the body temperature of the wearer exceeds a normal body temperature, thus indicating infection. The error code can trigger the generation of a warning message which can e.g. be displayed using the display means.

A warning indicator (not shown) can be provided on the healthcare garment 3, to which the generated error code or error codes can be communicated. Upon receipt of the error code, the warning indicator emits a warning signal, which could preferably be a visual or audio warning signal.

Apart from the first step S1 of providing a temperature sensor, all of the method steps, as well as any sub-sequence of steps, described above with reference to FIG. 2, may be controlled by means of a programmed computer. The invention thus also extends to computer programs, particularly computer programs provided on or in a carrier, adapted for putting the method into practice. The program may be in the form of source code or in any other form suitable for use in the implementation of the method according to the invention. The program may either be a part of an operating system, or be a separate application. The carrier may be any device capable of carrying the program. The carrier may e.g. comprise a storage medium, or it may be a transmissible carrier such as an electrical or optical signal which may be conveyed via electrical or optical cable, by radio, or by other means. Alternatively, the carrier may be an integrated circuit in which the program is embedded, the integrated circuit being adapted for performing, or for use in the performance of, the relevant steps.

The invention is of course not in any way restricted to the embodiments described above, but many possibilities to modifications thereof would be apparent to a person with skill in the art without departing from the scope of the invention as defined in the appended claims.

The invention claimed is:

1. A method for monitoring healthcare garments to prevent spread of hospital acquired infections, comprising the steps of:

providing a temperature sensor on or in a healthcare garment sensing the temperature of the healthcare garment by the temperature sensor, transferring temperature data relating to the sensed temperature over at least one network and a wireless interface from the temperature sensor to a base station, and in the base station, based on the temperature data, determining information relating to a usage cycle of said healthcare garment, wherein the step of determining information relating to the usage cycle of the healthcare garment includes comparing the temperature data to a predefined washing temperature value and at least one predefined temperature range associated with the usage cycle including at least one of a predefined wearing temperature range, and a predefined storage temperature range; and that the step of determining information relating to the usage cycle of the healthcare garment includes determining the amount of time spent in said wearing temperature range and/or in said storage temperature range without exceeding said washing temperature value, said method further comprising the steps of:

comparing said information relating to a usage cycle of said healthcare garment to at least one predefined warning condition, and given that said predefined warning condition is fulfilled, generating an error code.

2. The method according to claim 1, wherein said information relating to the usage cycle of said healthcare garment includes a body temperature of a wearer of said healthcare garment.

3. The method according to claim 2, wherein the step of determining information relating to a usage cycle of said healthcare garment further includes comparing the temperature data to an infection indicating range.

4. The method according to claim 2, further comprising the steps of:

providing a warning indicator on or in said healthcare garment, communicating said error code to the warning indicator, and in response to said error code, emitting a warning signal from the warning indicator.

5. A system for monitoring healthcare garments, comprising:

a temperature sensor provided on or in a healthcare garment, the temperature sensor being adapted to sense the temperature of said healthcare garment and to send temperature data relating to the sensed temperature over at least one network and a wireless interface, and a base station adapted to receive said temperature data, wherein the base station is configured to, on the basis of the received temperature data, determine information relating to a usage cycle of said healthcare garment by comparing the temperature data to a predefined washing temperature value and at least one predefined temperature range associated with the usage cycle, including at least one of a predefined wearing temperature range, and a predefined storage temperature range, and wherein the base station is configured to determine the amount of time spent in said wearing temperature range and/or in said storage temperature range without exceeding said washing temperature value.

6. The system according to claim 5, wherein the base station is configured to compare said information relating to a usage cycle of said healthcare garment to at least one predefined warning condition, and given that said predefined warning condition is fulfilled, generate an error code indicating a risk of spread of hospital acquired infections.

7. The system according to claim 6, further comprising a warning indicator provided on or in said healthcare garment, the warning indicator being configured to receive said generated error code from the base station and in response thereto emit a warning signal.

8. The system according to claim 5, wherein the step of providing the temperature sensor on or in the healthcare garment comprises mounting the temperature sensor in a neckband of the healthcare garment.

9. The system according to claim 5, wherein the base station is configured to, on the basis of the received temperature data, determine information relating to a usage cycle of said healthcare garment by further comparing the temperature data to an infection indicating range.

10. The system according to claim 1, wherein the error code indicates a risk of spread of hospital acquired infections based on said information relating to a usage cycle of said healthcare garment.

* * * * *